US011819507B2

(12) United States Patent
Salami et al.

(10) Patent No.: US 11,819,507 B2
(45) Date of Patent: Nov. 21, 2023

(54) CHOLECALCIFEROL SULFATE SALTS AND THEIR USE FOR THE TREATMENT OF VITAMIN D DEFICIENCY

(71) Applicant: CFSO GMBH, Geretsried (DE)

(72) Inventors: Oyewole Taye Salami, Wolfratshausen (DE); Sigrid Obenland, Munich (DE); Reinhard Caliebe, Doehlau O.T. Tauberlitz (DE)

( * ) Notice: Subject to any disclaimer, the term of this patent is extended or adjusted under 35 U.S.C. 154(b) by 1136 days.

(21) Appl. No.: 15/743,327

(22) PCT Filed: Jul. 12, 2016

(86) PCT No.: PCT/EP2016/001201
§ 371 (c)(1),
(2) Date: Jan. 10, 2018

(87) PCT Pub. No.: WO2017/008902
PCT Pub. Date: Jan. 19, 2017

(65) Prior Publication Data
US 2018/0200269 A1    Jul. 19, 2018

(30) Foreign Application Priority Data

Jul. 12, 2015  (DE) ............................ 102015009022
Nov. 15, 2015  (DE) ............................ 102015014760

(51) Int. Cl.

| A61K 31/593 | (2006.01) |
|---|---|
| A61K 9/00 | (2006.01) |
| A61K 9/08 | (2006.01) |
| A61K 9/10 | (2006.01) |
| A61K 47/02 | (2006.01) |
| A61K 47/14 | (2017.01) |
| A61P 43/00 | (2006.01) |
| A61K 9/70 | (2006.01) |
| A61K 31/198 | (2006.01) |
| A61K 47/10 | (2017.01) |
| A61K 47/44 | (2017.01) |
| C07C 401/00 | (2006.01) |

(52) U.S. Cl.
CPC ............ *A61K 31/593* (2013.01); *A61K 9/006* (2013.01); *A61K 9/0014* (2013.01); *A61K 9/0019* (2013.01); *A61K 9/08* (2013.01); *A61K 9/10* (2013.01); *A61K 9/7023* (2013.01); *A61K 31/198* (2013.01); *A61K 47/02* (2013.01); *A61K 47/10* (2013.01); *A61K 47/14* (2013.01); *A61K 47/44* (2013.01); *A61P 43/00* (2018.01); *A61K 2300/00* (2013.01)

(58) Field of Classification Search
CPC ............ A61K 2300/00; A61K 31/198; A61K 31/593; A61K 47/02; A61K 47/10; A61K 47/14; A61K 47/44; A61K 9/0014; A61K 9/0019; A61K 9/006; A61K 9/08; A61K 9/10; A61K 9/7023; A61P 43/00

USPC ........................................................ 514/167
See application file for complete search history.

(56) References Cited

U.S. PATENT DOCUMENTS

| 2,296,291 | A | * | 9/1942 | Milas ..................... C07C 401/00 552/653 |
| 2,584,731 | A | * | 2/1952 | Ogawa .................. C07C 227/40 562/573 |
| 2,791,606 | A | * | 5/1957 | Novak ................... C07C 227/40 562/573 |
| 3,139,378 | A | * | 6/1964 | Gooding ............... C07C 51/412 424/490 |
| 3,365,488 | A | * | 1/1968 | Fernholz ............... C07C 51/412 562/601 |
| 3,450,752 | A | * | 6/1969 | Inklaar .................. A23L 33/175 562/573 |
| 3,989,822 | A | * | 11/1976 | Whistler ............ A61K 31/7004 514/23 |
| 4,588,528 | A | * | 5/1986 | DeLuca ................ C07C 401/00 552/541 |
| 5,422,127 | A | * | 6/1995 | Dube ..................... A23G 3/346 426/73 |
| 5,478,816 | A | * | 12/1995 | Shah ..................... A61K 9/0095 514/167 |
| 2005/0192255 | A1 | * | 9/2005 | Tian ....................... A61K 31/59 514/167 |
| 2011/0152207 | A1 | * | 6/2011 | Goff ..................... A61K 31/592 514/25 |
| 2012/0003316 | A1 | * | 1/2012 | Reddy .................... A61K 9/006 424/487 |
| 2015/0250803 | A1 | * | 9/2015 | Goff ..................... A61K 31/592 514/25 |
| 2016/0304553 | A1 | * | 10/2016 | Baharaff .............. A61K 31/575 |

FOREIGN PATENT DOCUMENTS

WO    2003035027 A1 *  1/2003

OTHER PUBLICATIONS

Fuller et al. (JPEN J. Parenter Enteral Nutr: 2011; 35:757-762).*
Boulch et al. (Steroids. Apr. 1982;39(4):391-8).*
Alsaqr et al. (AAPS PharmSciTech. 2015 16(4): 963-972).*
S. Nagubandi et al. (The Journal of Biological Chemistry, vol. 256, No. 11, Issue of Jun. 10, pp. 5536-5539, 1981).*
C. G. Perrine et al: "Adherence to Vitamin D Recommendations Among US Infants", Pediatrics vol. 125. No. 4., Apr. 4, 2010 (Apr. 1, 2010), pp. 627-632.
Thomas A Lebbetter: "The Canadian Medical Association Journal". The Canadian Medical Association Journal. vol. 14. No. 12. Jan. 1, 1924 (Jan. 1, 1924), pp. 1179-1182.
Leonor Cancela et al: "Lack of biological activity of vitamin D 3-3[beta] sulfate during lactation in vitamin D-deficient rats". Reproduction. Nutrition. Development, vol. 27, No. 6, Jan. 1, 1987 (Jan. 1, 1987). pp. 979-997.
Boulch N L et al: "Cholecalciferol sulfate identification in human milk by HPLC". Steroids, Elsevier Science Publishers. New York, NY, US, vol. 39. No. 4, Apr. 1, 1982 (Apr. 1, 1982). pp. 391-398.

\* cited by examiner

*Primary Examiner* — Michael Barker
(74) *Attorney, Agent, or Firm* — Abel Schillinger, LLP

(57) ABSTRACT

Pharmaceutically acceptable cholecalciferol sulfate salts are used for combating vitamin $D_3$ deficiency. New cholecalciferol sulfate salts as well as pharmaceutical compositions of the pharmaceutically acceptable cholecalciferol sulfate salts are described as well.

20 Claims, 1 Drawing Sheet

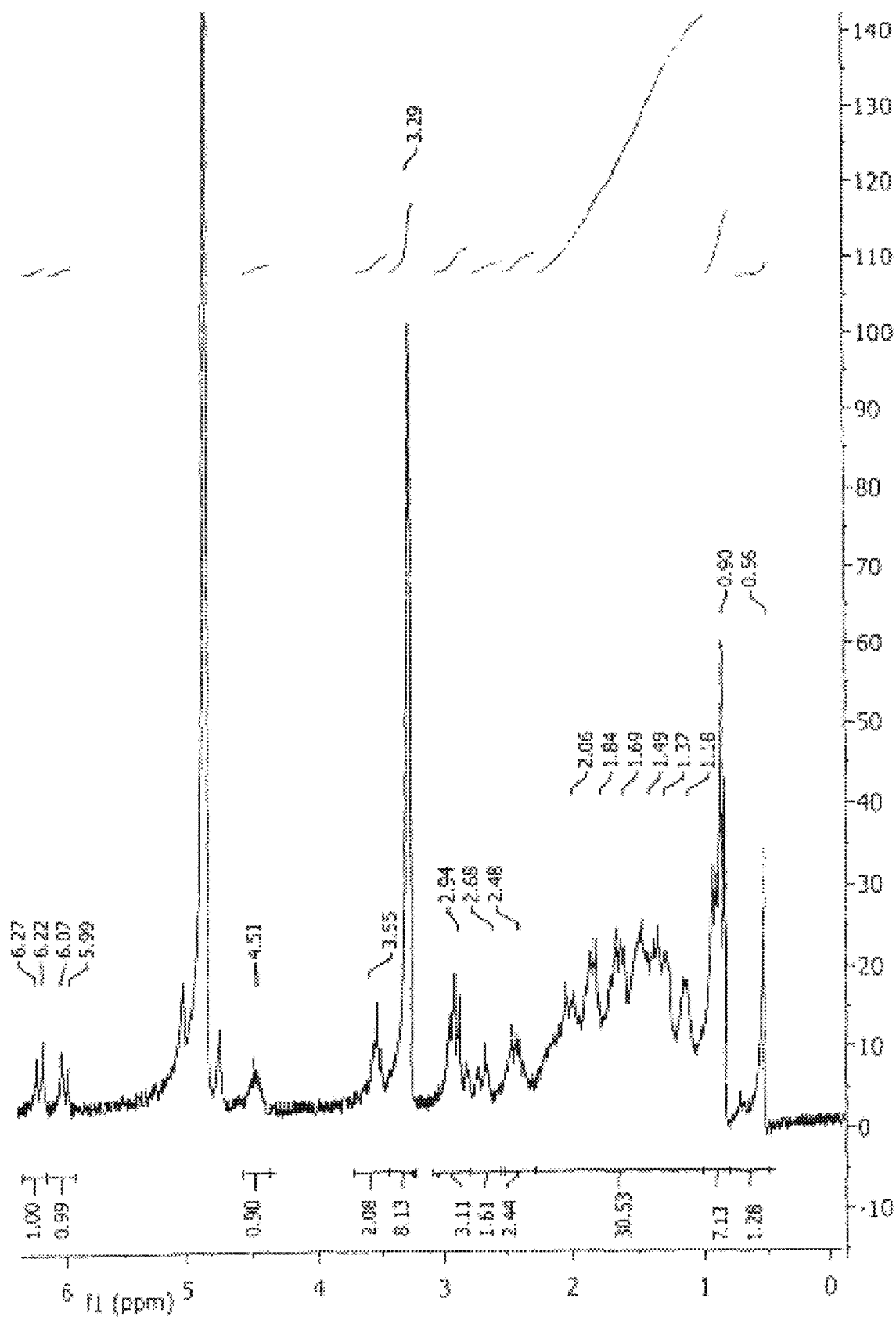
NMR spectrum (200 MHz; internal standard: TMS) of L-Lysine cholecalciferol sulfate in D$_4$-methanol

CHOLECALCIFEROL SULFATE SALTS AND THEIR USE FOR THE TREATMENT OF VITAMIN D DEFICIENCY

BACKGROUND OF THE INVENTION

Field of the Invention

This invention relates to the use of pharmaceutically acceptable cholecalciferol sulfate salts for combating vitamin $D_3$ deficiency in vertebrates and particularly humans by an administration method which effects that at least 5% of the cholecalciferol sulfate salts as such is supplied from the site of administration to a systemic fluid transport system of the human body without metabolization, to new pharmaceutically acceptable cholecalciferol sulfate salts as well as to pharmaceutical compositions for the above cited administration of dosage form, which contain pharmaceutically acceptable cholecalciferol sulfate salts.

Discussion of Background Information

It is known that a large fraction of the population of the world suffers from vitamin $D_3$ deficiency. Under natural conditions, vitamin $D_3$ is known to be produced in humans from 7-dehydrocholesterol by exposition of the skin to UV radiation as water soluble vitamin $D_3$ sulfate (cholecalciferol sulfate). Especially in the winter months many persons cannot expose themselves sufficiently to UV radiation for formation of sufficient amounts of vitamin $D_3$ sulfate in the skin.

Cholecalciferol sulfate is found in breast milk and in smaller amounts also in other kinds of milk. Some other types of food, such as cod liver oil, contain non-sulfated fat-soluble vitamin $D_3$ (cholecalciferol). In dietary supplements vitamin $D_3$ is also contained as fat-soluble cholecalciferol. This latter form of vitamin $D_3$ is not sulfated in the body.

The object of the invention was to achieve a supply of the body with natural cholecalciferol sulfate in a rapid or otherwise prolonged fashion without the necessity for irradiating the skin with UV radiation.

SUMMARY OF THE INVENTION

Accordingly, the invention relates to the use of pharmaceutically acceptable cholecalciferol sulfate salts for combating vitamin $D_3$ deficiency in vertebrates and especially humans by an administration method which effects that at least 5% of the cholecalciferol sulfate salts reach a systemic fluid transport system of the human body from the site of administration as such without metabolization.

Further the invention relates to new pharmaceutically acceptable cholecalciferol sulfate salts, especially cholecalciferol sulfate magnesium, cholecalciferol sulfate calcium and L-lysine-cholecalciferol sulfate.

Finally, the invention relates to a pharmaceutical composition which comprises at least one pharmaceutically acceptable cholecalciferol sulfate salt and a carrier suited for transdermal or transmucosal administration or intradermal, subcutaneous or intramuscular injection.

BRIEF DESCRIPTION OF THE DRAWING

FIG. 1 shows the NMR spectrum (200 MHz; internal standard: TMS) of L-lysine cholecalciferol sulfate in $D_4$-methanol.

DETAILED DESCRIPTION

Surprisingly, it was found that cholecalciferol sulfate salts and thus, vitamin $D_3$ in its native form can be supplied to the body in a way without immediate metabolization thereof into water-insoluble cholecalciferol or (25OH)-cholecalciferol. The lymph system is able to distribute the water-soluble cholecalciferol sulfate salts as such in the body. The water-soluble cholecalciferol sulfate salts are of course also soluble in blood. However, there they may potentially undergo rapid, e.g. enzymatic, decomposition.

Herein, combating vitamin $D_3$ deficiency means prevention and treatment of vitamin $D_3$ deficiency.

Pharmaceutically acceptable cholecalciferol sulfate salts herein means that the cations of these salts are in no way toxic for the human body. Pharmaceutically acceptable cations are for example Na, Mg, Ca, Zn, Ammonium, and protonated amino acids, such as protonated lysine.

Cholecalciferol sulfate salts are usually soluble in water or an aqueous-alcoholic mixture. Examples for pharmaceutically acceptable cholecalciferol sulfate salts with an inorganic cation are sodium cholecalciferol sulfate, magnesium cholecalciferol sulfate, calcium cholecalciferol sulfate and ammonium cholecalciferol sulfate. Examples for pharmaceutically acceptable cholecalciferol sulfate salts with organic cations are trimethylammonium cholecalciferol sulfate and L-lysine cholecalciferol sulfate The method of administration in accordance with the present invention is chosen such that it effects that at least 5% of the administrated amount of cholecalciferol sulfate salt is transported from the site of administration into a systemic fluid transport system of the human body without metabolization. Depending on the method of administration, preferably at least 10%, 15%, 20%, 25%, 30%, 35%, 40%, 45% or 50% of the administered cholecalciferol sulfate salt reach a systemic fluid transport system of the human body from the site of administration as such without experiencing metabolization.

Preferably, the administered cholecalciferol sulfate salt is chemically modified (metabolized) by less than 70%, preferably less than 60%, e.g. 50%, 40%, 30%, 20% or even less than 10% or less in at least one of the systemic fluid transport systems selected from blood and lymph over a time period of at least 5 minutes, preferably more than at least 10, 15, 20 or even 30 minutes being.

Systemic fluid transport systems of the human body are e.g. blood and preferably lymph.

Preferred ways of administration for the pharmaceutically acceptable cholecalciferol sulfate salts are transdermal or transmucosal administration as well as the intradermal, subcutaneous and intramuscular injection, depot-injections with prolonged release of the active substance being included. Peroral administration (i.e. supplied to the stomach e.g. by swallowing), intravenous and intra-arterial injection are explicitly excluded as ways of administration.

The molar amount of the cholecalciferol sulfate salts administered generally corresponds to the molar amounts recommended for cholecalciferol.

The preparation of the cholecalciferol sulfate salts can be effected by reacting commercial cholecalciferol with pyridine-sulphur trioxide complex in pyridine and subsequent reaction with triethylamine to triethylammonium cholecalciferol sulfate, which then can be reprecipitated in aqueous solution by adding saturated solutions of appropriate cations so as to form salts together with these cations.

Alternatively, cholecalciferol can be reacted with pyridine-sulphur trioxide complex in pyridine and then be directly reacted with the desired cation, optionally in presence of an appropriate buffer, to form the desired salt.

The pharmaceutical compositions in accordance with the invention comprise a suitable carrier or a suitable vehicle. They can also comprise additional active agents, such as other vitamins, minerals and trace elements as well as medicaments of any kind.

Suitable vehicles or carriers for transdermal administration are all vehicles known to the person skilled in the art in the field of pharmacy for this purpose. These comprise liquid or solid vehicles on fat or oil basis as well as vehicles on aqueous are aqueous-alcoholic basis. The formulations can take the form of ointments and oils, lotions, solutions adapted for being sprayed, suspensions and emulsions of any kind, and patches which contain the active substance in a vehicle. The formulations can comprise penetration enhancers, such as dimethylsulfoxide, emulsifiers as well as any further excipients commonly used in pharmacy, such as diluents, flavoring agents, solubilizers, lubricating agents, suspending agents, binders and preservatives.

Suitable formulations for transmucosal administration are for example, aqueous or alcoholic-aqueous solutions which may comprise further excipients, suppositories on a fat basis, creams, gels, pastes, foams or sprays and pessars and tamponade suited for vaginal administration as well as solid dosage forms suitable for topical administration in the mouth or sublingual administration including lozenges containing the active component in a flavored base, normally sucrose and acacia gum or tragacanth; pastilles, containing the active component in an inert base such as gelatin or glycerol; and chewing gums. Formulations for transmucosal administration can also comprise penetration enhancers such as dimethyl sulfoxide, emulsifiers as well as any further excipients common in pharmacy.

Preparations in liquid form for parenteral administration by means of intradermal, subcutaneous and intramuscular injection include suspensions, solutions or emulsions in oily or aqueous vehicles. The preparations can comprise formulation excipients, such as suspending agents, stabilizing agents and/or dispersing agents. Alternatively, the active component may be in the form of powder which is mixed with an appropriate vehicle like sterile pyrogen-free water for constitution thereof before use.

A detailed presentation of forms of administration suitable for use in the present invention can be found for example in Remington, The Science and Practice of Pharmacy, Ed. Allen, Loyd V. Jr, 22nd Edition, Pharmaceutical Press.

EXAMPLES

Example 1—Preparation of Triethylammonium Cholecalciferol Sulfate 6.5 ml of pyridine were added to 1.21 g pyridine-sulphur trioxide complex (ca. 6.76 mmol pyridine complexed with $SO_3$; Sigma-Aldrich; ≥45 wt.-% $SO_3$ according to information by the manufacturer) and 1.21 g (3.14 mmol) cholecalciferol (Sigma-Aldrich) under a nitrogen atmosphere. The solution obtained was intensively stirred for 1 h at 58° C. Then 0.63 ml (0.456 g; 4.55 mmol) of triethylamine were added and stirring was continued for further 20 min. at 58° C.

Then the reaction mixture was cooled in an ice bath at 0° C., 16.5 ml of a cold methanol-trichloromethane (10:1 vol./vol.) solution were added and stirring was continued for 20 min.

The solution was filtered through a glass frit and the solvent was removed on a rotary evaporator. For further purification the residue was twice treated with methanol-trichloromethane (10:1 Vol./Vol.) solution and the solvent was removed on a rotary evaporator, thereby obtaining 1.52 g (3.13 mmol; 99.7%) of triethylammonium cholecalciferol sulfate.

TLC (silica gel): $R_F$=0.42 in methanol-trichloromethan (1:9 vol./vol.).

Example 2—Preparation of Ammonium Cholecalciferol Sulfate

About 14 ml of saturated ammonium acetate solution were added to 1.52 g (3.13 mmol) of triethylammonium cholecaliferol sulfate until a white precipitate of ammonium cholecalciferol sulfate formed, which after having been left standing over night was filtered using a glass frit and dried under high vacuum while being cooled by tap water at a temperature of about 15° C.

Yield: 1.74 g (3.10 mmol, 99%).
Melting point 104-108° C.

Example 3—Preparation of Sodium Cholecalciferol Sulfate

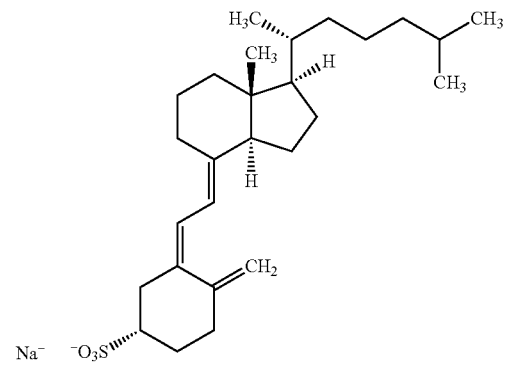

A saturated solution of sodium chloride (ca. 14 ml) was added to 1.52 g (3.13 mmol) of triethylammonium cholecalciferol sulfate until a white precipitate of sodium cholecalciferol sulfate formed, which after having been left standing over night was filtered using a glass frit and dried under high vacuum while being cooled by tap water having a temperature of about 15° C.

Yield: 1.75 g (3.10 mmol, 99%).

The NMR-Spektrum was identical to the one published in L. E. Reeve et al., The Journal of Biological Chemistry (1981) Vol. 256, Nr. 2, p. 824.

Example 4—Preparation of Magnesium Cholecalciferol Sulfate

A saturated solution of magnesium chloride (ca.13 ml) was added to 1.52 g (3.13 mmol) of triethylammonium cholecaliferol sulfate until a white precipitate of magnesium cholecalciferol sulfate formed, which after having been left standing over night was filtered using a glass frit and dried under high vacuum while being cooled by tap water having a temperature of about 15° C.

Yield: 1.76 g (3.10 mmol; 99%).
Melting point: 107-110° C. (decomposition).

Example 5—Preparation of Calcium Cholecalciferol Sulfate

A saturated solution of $CaCl_2 \cdot 2H_2O$ (ca. 13 ml) was added to 1.52 g (3.13 mmol) of triethylammonium cholecaliferol sulfate until a white precipitate of calcium cholecalciferol sulfate formed, which after having been left standing over night was filtered using a glass frit and dried under high vacuum while being cooled by tap water having a temperature of about 15° C.

Yield: 1.81 g, (3.10 mmol, 99%).

TLC(silica gel): $R_f$=0.48 in methanol-trichloromethane (1:9 Vol./Vol.)

Melting point: 97-101° C. (decomposition.).

Example 6—Preparation of L-Lysine Cholecalciferol Sulfate

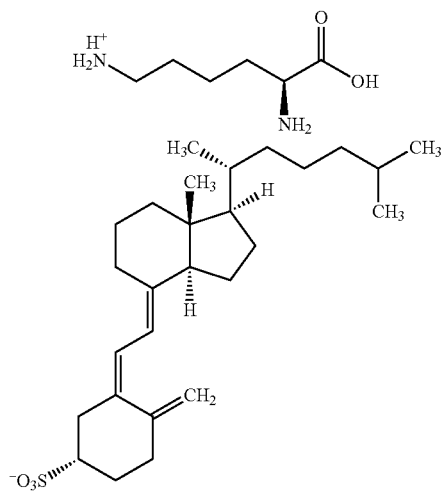

517.4 mg of pyridine-sulphur trioxide complex (Sigma-Aldrich; ≥45 Wt.-% $SO_3$ according to information by the manufacturer) (ca. 2.90 mmol of pyridine complexed with $SO_3$) und 506.3 mg (1.32 mmol) of cholecaliferol (Sigma-Aldrich) were dissolved in 4.4 ml pyridine under a nitrogen atmosphere and heated at 55° C. for 1 h while being vigorously stirred. After addition of 10 ml of ice-cooled methanol-trichloromethane (1:9 Vol/Vol) mixture the solvents were removed on a rotary evaporator. Then 0.29 g L-lysine (1.98 mmol) in 0.5 ml of sodium phosphate buffer solution, pH 7.3, was added and stirred for 5 min. Then 20 ml of ice-cooled methanol-trichloromethane (1:9 vol./vol.) mixture was added while stirring, thereafter the mixture was stripped on a rotary evaporator. 10 ml of absolute ethanol was added to the residue, and the solution was stored over night in a refrigerator. Then the ethanol was decanted from the white creamy precipitate formed and the residue was dried while being cooled by tap water at a temperature of about 15° C., whereby the title compound was obtained as a white powder (815 mg, (1.30 mmol); 98.5%).

TLC (silica gel): $R_f$=0.33 in methanol-trichloromethane (1:9 Vol./Vol.).

Melting point: 168° C. (decomposition)

NMR spectrum: see FIG. 1

Example 7—Preparation of D,L-Lysine Cholecalciferol Sulfate

The preparation of D,L-lysine cholecalciferol sulfate is effected in a way analogous to the preparation of L-lysine cholecalciferol sulfate using DL-lysine (Sigma.-Aldrich) instead of L-lysine.

The NMR spektrum in $D_4$-methanol confirms the structure.

Example 8—Transdermal Formulation of L-Lysine Cholecalciferol Sulfate in an Oil Base 100 mg of L-lysine cholecalciferol sulfate were mixed with 11.04 ml of oleic acid, then 0.83 ml of dimethylsulfoxide were added and stirred by a magnetic stirrer for 2 days at room temperature (21-25° C.). Subsequently, 10 ml of glycerol trioleate and 7 ml of glycerol momonooleate (Pecerol®, Gattefosse) were added and vigorously shaken. After waiting until the mixture was defoamed, an almost completely clear stable solution of L-lysine chole-calciferol sulfate in the oil phase was obtained.

Example 9—Applying the Transdermal Formulation of Example 8 to Skin

About 2 ml of the formulation prepared in Example 8 were applied in a thin layer to the skin of a subject and allowed to penetrate for 4 hours. Subsequently, the skin was well wiped using a sterile cotton pad soaked with 96% ethanol. The cotton pad was boiled with additional 96% ethanol and squeezed. The ethanol was evaporated on a rotary evaporator, and a small amount of chloroform-methanol (9:1 Vol./Vol.) mixture was added to the flask. TLC of this mixture on silica gel showed that substantially no L-lysine cholecalciferol sulfate ($R_f$: 0.33) had remained on the skin.

Example 10—Preparation of Aqueous Injection Solutions

For preparing a 2 ml injection solution containing the cholecalciferol sulfate salt in an amount corresponding to 10.000 IE of vitamin $D_3$
 a) 1.5695 mg sodium cholecalciferol sulfate for producing the injection solution A
 b) 1.6243 mg calcium cholecalciferol sulfate for producing the injection solution B and
 c) 1.970 mg L-lysine cholecalciferol sulfate for producing the injection solution C were each dissolved in 10 ml of distilled water. Then 89.9028 mg sodium chloride was added to each of the solutions to render them isotonic.

The pH of the injection solutions B was adjusted to pH 7 using 0.5N NaOH.

Thereafter the solutions were filter-sterilized under argon atmosphere through a 0.22 µm membrane and filled into 2 ml vials.

The disclosure of all documents cited herein, such as patents, published patent applications, papers published in journals and books, is hereby incorporated in its entirety into this specification by reference.

What is claimed is:
1. A pharmaceutically acceptable salt of cholecalciferol sulfate, wherein the salt is different from sodium cholecal- ciferol sulfate, ammonium cholecalciferol sulfate and trimethylammonium cholecalciferol sulfate.

2. The pharmaceutically acceptable salt of claim 1, which is magnesium cholecalciferol sulfate.

3. The pharmaceutically acceptable salt of claim 1, which is calcium cholecalciferol sulfate.

4. The pharmaceutically acceptable salt of claim 1, which is L-lysine cholecalciferol sulfate.

5. A pharmaceutical composition, wherein the composition comprises at least one pharmaceutically acceptable salt of cholecalciferol sulfate that is different from sodium cholecalciferol sulfate, ammonium cholecalciferol sulfate and trimethylammonium cholecalciferol sulfate and a vehicle which is suitable for at least one of transdermal administration, transmucosal administration, intradermal injection, subcutaneous injection, and intramuscular injection.

6. The composition of claim 5, wherein the vehicle is an oil- or fat-based vehicle which is suitable for transdermal administration.

7. The composition of claim 5, wherein the vehicle is an aqueous or aqueous-alcoholic vehicle which is suitable for transdermal administration.

8. The composition of claim 5, wherein the composition is present as a patch.

9. The composition of claim 5, wherein the vehicle is suitable for transmucosal administration on an aqueous or aqueous-alcoholic basis.

10. The composition of claim 5, wherein the vehicle is an aqueous or aqueous-alcohol-based vehicle suitable for intradermal, subcutaneous or intramuscular injection.

11. The composition of claim 5, wherein the at least one pharmaceutically acceptable salt of cholecalciferol sulfate comprises L-lysine cholecalciferol sulfate.

12. The composition of claim 11, wherein the vehicle is an oil- or fat-based vehicle which is suitable for transdermal administration.

13. The composition of claim 11, wherein the vehicle is an aqueous or aqueous-alcoholic vehicle which is suitable for transdermal administration.

14. The composition of claim 11, wherein the composition is present as a patch.

15. The composition of claim 11, wherein the vehicle is suitable for transmucosal administration on an aqueous or aqueous-alcoholic basis.

16. The composition of claim 11, wherein the vehicle is an aqueous or aqueous-alcohol-based vehicle suitable for intradermal, subcutaneous or intramuscular injection.

17. A method of combating vitamin $D_3$ deficiency in vertebrates, wherein the method comprises administering to a vertebrate in need thereof the pharmaceutical composition of claim 5.

18. The method of claim 17, wherein the administration method is selected from transdermal, transmucosal, intradermal, subcutaneous, and intramuscular injection.

19. The method of claim 17, wherein the administration method comprises transdermal administration.

20. The method of claim 17, wherein the administration method comprises transmucosal administration.

* * * * *